(12) United States Patent
Pettit

(10) Patent No.: US 6,578,963 B2
(45) Date of Patent: Jun. 17, 2003

(54) WAVEFRONT SENSOR FOR OBJECTIVE MEASUREMENT OF AN OPTICAL SYSTEM AND ASSOCIATED METHODS

(75) Inventor: George H. Pettit, Maitland, FL (US)

(73) Assignee: Alcon Universal Ltd., Hunenberg (CH)

( * ) Notice: Subject to any disclaimer, the term of this patent is extended or adjusted under 35 U.S.C. 154(b) by 134 days.

(21) Appl. No.: 09/838,669

(22) Filed: Apr. 19, 2001

(65) Prior Publication Data

US 2002/0003606 A1 Jan. 10, 2002

Related U.S. Application Data

(60) Provisional application No. 60/198,536, filed on Apr. 19, 2000.

(51) Int. Cl.[7] .................................................. A61B 3/10
(52) U.S. Cl. ........................................................ 351/212
(58) Field of Search ........................... 351/211, 212, 351/216, 220, 221; 359/1, 19, 20, 109, 115, 117

(56) References Cited

U.S. PATENT DOCUMENTS

| | | | |
|---|---|---|---|
| 3,679,904 A | * | 7/1972 | Weiner ........................ 359/117 |
| 3,880,501 A | | 4/1975 | Munnerlyn |
| 4,069,823 A | | 1/1978 | Isakov et al. |
| 4,523,821 A | | 6/1985 | Lang et al. |
| 4,579,430 A | | 4/1986 | Bille |
| 4,632,528 A | | 12/1986 | Yoshino et al. |
| 4,669,466 A | | 6/1987 | L'Esperance |
| 4,688,941 A | | 8/1987 | Philbert |
| 4,702,245 A | | 10/1987 | Schröder et al. |
| 4,718,418 A | | 1/1988 | L'Esperance, Jr. |
| 4,721,379 A | | 1/1988 | L'Esperance |
| 4,729,372 A | | 3/1988 | L'Esperance, Jr. |
| 4,750,818 A | | 6/1988 | Cochran |
| 4,764,930 A | | 8/1988 | Bille et al. |
| 4,838,679 A | | 6/1989 | Bille |
| 4,848,340 A | | 7/1989 | Bille et al. |
| 4,881,808 A | | 11/1989 | Bille et al. |

(List continued on next page.)

FOREIGN PATENT DOCUMENTS

| | | |
|---|---|---|
| DE | 42 22 395 A1 | 1/1994 |
| DE | 199 26 476 A1 | 12/2000 |
| EP | 0 697 611 A3 | 2/1996 |
| EP | 0 697 611 A2 | 2/1996 |
| FR | 2 775 779 | 9/1999 |
| JP | 5-146409 | 6/1993 |
| JP | 6-327634 | 11/1994 |
| WO | WO 87/05205 | 9/1987 |
| WO | WO 87/06478 | 11/1987 |
| WO | WO 92/01417 | 2/1992 |
| WO | WO 95/28989 | 11/1995 |
| WO | WO 98/27863 | 7/1998 |

OTHER PUBLICATIONS

Reidy, et al., "Corneal Topography of Epikeratophakia," *Refractive & Corneal Surgery*, vol. 6, Jan./Feb. 1990, pp. 26–31.

*Primary Examiner*—George Manuel
(74) *Attorney, Agent, or Firm*—Allen, Dyer, Doppelt, Milbrath & Gilchrist, P.A.

(57) ABSTRACT

A wavefront sensor includes an afocal relay stage for magnifying an incoming wavefront reflected from a source plane. In an exemplary application, a retina of an eye reflects an impinging light beam thereon to form a series of wavefronts. A lenslet array is positioned at a reference plane of the afocal relay stage to receive the magnified wavefront. Further downstream is positioned a means for imaging and demagnifying a focal plane image of the lenslet array at a final image plane. This demagnified image then serves as input to an analyzer, such as a charge-coupled-device (CCD) camera.

20 Claims, 1 Drawing Sheet

U.S. PATENT DOCUMENTS

| | | |
|---|---|---|
| 4,901,718 A | 2/1990 | Bille et al. |
| 4,907,586 A | 3/1990 | Bille et al. |
| 4,941,093 A | 7/1990 | Marshall et al. |
| 4,972,836 A | 11/1990 | Schenck et al. |
| 4,988,348 A | 1/1991 | Bille |
| 4,991,953 A | 2/1991 | Pflibsen et al. |
| 5,026,977 A | 6/1991 | Hubbard, Jr. |
| 5,062,702 A | 11/1991 | Bille |
| 5,106,183 A | 4/1992 | Yoder, Jr. |
| 5,114,628 A | 5/1992 | Höfer et al. |
| 5,139,022 A | 8/1992 | Lempert |
| 5,147,352 A | 9/1992 | Azema et al. |
| 5,159,361 A | 10/1992 | Cambier et al. |
| 5,177,511 A | 1/1993 | Feuerstein et al. |
| 5,184,157 A | 2/1993 | Ichihashi et al. |
| 5,196,006 A | 3/1993 | Klopotek et al. |
| 5,198,845 A | 3/1993 | Triller |
| 5,202,709 A | 4/1993 | Ichihashi et al. |
| 5,214,456 A | 5/1993 | Gersten |
| 5,221,834 A | 6/1993 | Lisson et al. |
| 5,229,889 A | 7/1993 | Kittell |
| 5,233,174 A | 8/1993 | Zmek |
| 5,243,367 A | 9/1993 | Spellitz |
| 5,246,435 A | 9/1993 | Bille et al. |
| 5,258,791 A | 11/1993 | Penney et al. |
| 5,263,950 A | 11/1993 | L'Esperance, Jr. |
| 5,279,611 A | 1/1994 | McDonnell et al. |
| 5,293,871 A | 3/1994 | Reinstein et al. |
| 5,298,971 A | 3/1994 | Huang et al. |
| 5,307,097 A | 4/1994 | Baker |
| 5,324,281 A | 6/1994 | Muller |
| 5,334,190 A | 8/1994 | Seiler |
| 5,339,121 A | 8/1994 | Shimmick et al. |
| 5,360,424 A | 11/1994 | Klopotek |
| 5,395,356 A | 3/1995 | King et al. |
| 5,404,884 A | 4/1995 | Lempert |
| 5,410,376 A | 4/1995 | Cornsweet et al. |
| 5,411,501 A | 5/1995 | Klopotek |
| 5,423,801 A | 6/1995 | Marshall et al. |
| 5,437,658 A | 8/1995 | Muller et al. |
| 5,439,462 A | 8/1995 | Bille et al. |
| 5,442,412 A | 8/1995 | Frey et al. |
| 5,452,031 A | 9/1995 | Ducharme |
| 5,461,212 A | 10/1995 | Seiler et al. |
| 5,473,392 A | 12/1995 | Klopotek |
| 5,474,548 A | 12/1995 | Knopp et al. |
| 5,475,452 A | 12/1995 | Kuhn et al. |
| 5,491,524 A | 2/1996 | Hellmuth et al. |
| 5,493,391 A | 2/1996 | Neal et al. |
| 5,502,518 A | 3/1996 | Lieberman |
| 5,505,723 A | 4/1996 | Muller |
| 5,507,741 A | 4/1996 | L'Esperance, Jr. |
| 5,512,965 A | 4/1996 | Snook |
| 5,512,966 A | 4/1996 | Snook |
| 5,521,657 A | 5/1996 | Klopotek |
| 5,548,354 A | 8/1996 | Kasahara et al. |
| 5,556,395 A | 9/1996 | Shimmick et al. |
| 5,563,709 A | 10/1996 | Poultney |
| 5,570,142 A | 10/1996 | Lieberman |
| 5,581,347 A | 12/1996 | Le Saux et al. |
| 5,592,246 A | 1/1997 | Kuhn et al. |
| 5,629,765 A | 5/1997 | Schmutz |
| 5,632,282 A | 5/1997 | Hay et al. |
| 5,632,742 A | 5/1997 | Frey et al. |
| 5,673,096 A | 9/1997 | Dorsel et al. |
| 5,684,545 A | 11/1997 | Dou et al. |
| 5,711,762 A | 1/1998 | Trokel |
| 5,722,427 A | 3/1998 | Wakil et al. |
| 5,735,283 A | 4/1998 | Snook |
| 5,735,843 A | 4/1998 | Trokel |
| 5,740,803 A | 4/1998 | Gray et al. |
| 5,757,463 A | 5/1998 | Kohayakawa |
| 5,777,719 A | 7/1998 | Williams et al. |
| 5,784,146 A | 7/1998 | Nanjo et al. |
| 5,785,704 A | 7/1998 | Bille et al. |
| 5,822,035 A | 10/1998 | Bille |
| 5,825,476 A | 10/1998 | Abitol et al. |
| 5,841,511 A | 11/1998 | D'Souza et al. |
| 5,847,804 A | 12/1998 | Sarver et al. |
| 5,861,955 A | 1/1999 | Gordon |
| 5,864,381 A | 1/1999 | Neal et al. |
| 5,920,373 A | 7/1999 | Bille |
| 5,929,970 A | 7/1999 | Mihashi |
| 5,936,720 A | 8/1999 | Neal et al. |
| 5,943,117 A | 8/1999 | Van De Velde |
| 5,949,521 A | 9/1999 | Williams et al. |
| 5,963,300 A | 10/1999 | Horwitz |
| 5,966,197 A | 10/1999 | Yee |
| 5,994,687 A | 11/1999 | Chanteloup et al. |
| 6,007,204 A | 12/1999 | Fahrenkrug et al. |
| 6,043,885 A | 3/2000 | Mazuet et al. |
| 6,050,687 A | 4/2000 | Bille et al. |
| 6,057,913 A | 5/2000 | Brown et al. |
| 6,086,204 A | 7/2000 | Magnante |
| 6,095,651 A | 8/2000 | Williams et al. |
| 6,155,684 A | 12/2000 | Bille et al. |

OTHER PUBLICATIONS

Dingeldein, et al., "The Topography of Normal Corneas," *Arch. Ophthalmol*, vol. 107, Apr. 1989, pp. 512–518.

McDonnell, et al., "Topographic Analysis and Visual Acuity After Radial Keratotomy," *American Journal of Ophthalmology*, vol. 106, No. 6, Dec. 1988, pp. 692–695.

McDonnell, et al., "Corneal Topographic Changes After Radial Keratotomy," *Ophthalmology*, vol. 96, No. 1, Jan. 1989, pp. 45–49.

Kiely, et al., "The Mean Shape of the Human Cornea," *Optica Acta*, vol. 29, No. 8, 1982, pp. 1027–1040.

Bafna, et al., "Corneal Power Calculated by the Paraxial Formula and Snell's Law in Normal Corneas," *Investigative Ophthalmology & Visual Science*, vol. 37, No. 3, Feb. 1996, Poster No. 2589.

Matallana, et al, "3–D Video Corneal Topography True Elevation Mapping," *Investigative Ophthalmology & Visual Science*, vol. 37, No. 3, Feb. 1996, Poster No. 2590.

Aoyama, et al, "Quantitative Evaluation of Corneal Astigmatism Using Computer Corneal Topography and Newly Developed Software," *Investigative Ophthalmology & Visual Science*, vol. 37, No. 3, Feb. 1996, Poster No. 2591.

Celikkol, et al, "Neural Network Analysis of Videokeratography Following Excimer Laser Photorefractive Keratectomy," *Investigative Ophthalmology & Visual Science*, vol. 37, No. 3, Feb. 1996, Poster No. 2592.

Walsh, et al., "Objective Technique for the Determination of Monochromatic Aberrations of the Human Eye," *J. Opt. Soc. Am. A*, vol. 1, No. 9, Sep. 1984, pp. 987–992.

Williams, et al., "Adaptive Optics for High Resolution Retinal Imaging," *Investigative Ophthalmology & Visual Science*, vol. 37, No. 3, Feb. 1996, p. 1055.

Charman, "Wavefront Aberration of the Eye: A Review," *Optometry and Vision Science*, vol. 68, No. 8, pp. 574–583.

Bartsch, et al., "Resolution Improvement in Confocal Scanning Laser Tomography of the Human Fundus," *1994 Technical Digest Series*, vol. 2 (Optical Society of America, Washington D. C.), 1994, pp. 134–137.

Dreher, et al., "Active Optical Depth Resolution Improvement of the Laser Tomographic Scanner," *Applied Optics,* vol. 28, No. 4, Feb. 1989, pp. 804–808.

Bille, et al., "Scanning Laser Tomography of the Living Human Eye," *Noninvasive Diagnostic Techniques in Ophthalmology,* Chapter 28, edited by Masters, B.R., Springer–Verlag, 1990, pp. 528–547.

Liang, Junzhong, *A New Method to Precisely Measure the Wave Aberrations of the Human Eye with a Hartmann–Shack Wavefront Sensor,* Inaugural Dissertation, Dec. 1991, pp. 1–115, Heidelberg, Germany.

Bille, et al., "Imaging of the Retina by Scanning Laser Tomography," *New Methods in Microscopy and Low Light Imaging,* vol. 1161, 1989, pp. 417–425.

Cubalchini, "Modal Wave–front Estimation from Phase Derivative Measurements," *J. Opt. Soc. Am.,* vol. 69, 1979, pp. 972–977.

"Modal Wave–front Estimation from Phase Derivative Measurements," Referenced in Bille, U.S. Patent No. 5,062,702 IDS, 1990.

Freischlad, et al., "Modal Estimation of a Wave Front from Difference Measurements Using the Discrete Fourier Transform," *J. Opt. Soc. Am.,* vol. 3, No. 11, Nov. 1986, pp. 1852–1861.

Klyce, et al., "Imaging, Reconstruction, and Display of Corneal Topography," *New Methods in Microscopy and Low Light Imaging,* vol. 1161, 1989, pp. 409–416.

Baker, "Optical Surface Testing of the Cornea," *New Methods in Microscopy and Low Light Imaging,* vol. 1161, 1989, pp. 427–437.

Southwell, "Wave–front Estimation from Wave–front Slope Measurements," *J. Opt. Soc. Am.,* vol. 70, No. 8, Aug. 1980, pp. 998–1005.

Kasper et al., "Increasing the Sensitivity of a Shack–Hartmann Sensor," Canterbury 1999, pps. 1–6 XP–002181681. http://www.mpia–hd.mpg.de/MPIA/Projects/ALFA/PAPERS/canterbury99MEK.pdf.

Takeuchi et al., "Wavefront Distortion Measurement of a SR Extraction Mirror for the Beam Profile Monitor Using Shack–Hartmann Method," Canada 1998, pps. 859–861, vol. 1, XP–002181680.

Liang et al., "Aberrations and Retinal Image Quality of the Normal Human Eye," J. Opt. Soc. Am. A, Nov. 1997, pps. 2873–2883, vol. 14, No. 11.

Hamam, H., "A Direct Technique for Calculating the Profile of Aberration of the Eye Measured by a Modified Hartmann–Shack Apparatus," Optics Communications 173, 2000, pp. 23–36.

Pulianto, et al., "High–Speed Photography of Excimer Laser Ablation of the Cornea," *Arch Ophithalmol,* vol. 105, Sep. 1987, pp. 1255–1259.

Liang, et al., "Objective Measurement of Wave Aberrations of the Human Eye with the Use of a Hartmann–Shack Wave–front Sensor," *J. Opt. Soc. Am. A,* vol. 11, No. 7, Jul. 1994, pp. 1949–1957.

Wu, "Supernormal Vision, a Focus on Adaptive Optics Improves Images of the Eye and Boosts Vision," *Science News,* vol. 152, Nov. 15, 1997, pp. 312–313.

Dreher, et al., "Active Optical Depth Resolution Improvement of the Laser Tomographic Scanner," *Applied Optics,* vol. 28, No. 4, Feb. 1989, pp. 804–808.

Geary, "Appendix 1.1 –Basic Geometrical Optics, Chapter 6 –Indirect Wavefront Measurement, Part II,"and "Chapter 7 –Wavefront Sensor Characterization & Calibration," *Introduction to Wavefront Sensors,* May 1995, pp. 10–11, 89–103, and 105–109.

"Scientists Snap Sharpest Pictures of Living Human Retina, "*http://www.rochester.edu/releases/opt/will.htm.* Oct. 3, 1994.

THE APPLIED OPTICS GROUP, "Shack Hartmann Sensors," *http://op.ph.ic.ac.uk/ao/sh sense.html* Jun. 4, 1996, pp. 1–3.

THE APPLIED OPTICS GROUP, "Astronomical Imaging Through Turbulence: An Overview,"http://op.ph.ic.ac.uk/ao/overview.html, Jun. 4, 1996, pp. 1–4.

.eESA,WFS, "Wave Front Sensor," *http://esapub.esrin.esa.it/pointtotest/test251.html,* May 23, 1997, pp. 1–2.

Williams, "Limits of Human Vision," *http://www.cvs.rochester.edu/people/d williams/d williams.html,* Dec. 30, 1998, pp. 1–4.

"Extensions of Low–Cost Adaptive Optics: Imaging of Space–Objects, the Retina, and Power Projection," Industrial Sensors and Actuators, dated Dec. 1993 (actual publication date, if any, unknown), pp. 1, 10, and 15.

Labjuhn, et al., Astigmatismuskorrektur durch Laserthermokeratoplastik (LTK)–Ein Ansatz für die Korrektur des hohen Astigmatismus nach perforierender Keratoplasti, *Contactologia 18D* (1996), pp. 175–183.

Cohen, et al., "Assessment of the Power and Height of Radial Aspheres Reported by a Computer–assisted Keratoscope," *American Journal of Ophthalmology,* vol. No. 6, Nov. 30, 1994, pp. 723–732.

Corbett, et al., "The Topography of the Normal Cornea," *Eur J Implant Ref Surg.,* vol. 6, Oct. 1994, pp. 286–297.

Maeder, et al., "Accurate 3D Corneal Surface Measurement Using an Automated Mapping Approach," SPIE, vol. 2434, 1995, pp. 328–334.

Salmon et al., "Comparison of Elevation, Curvature, and Power Descriptors for Corneal Topographic Mapping," *Optometry & Vision Science,* vol. 72, No. 11, 1195, pp. 800–808.

Pavlopoulos, et al., "The Effect of Artificial Tears on Computer–assisted Corneal Topography in Normal Eyes and After Penetrating Keratoplasty," *American Journal of Ophthalmology,* vol. 119, Jun. 1995, pp. 712–722.

Roberts, "Characterization of the Inherent Error in Spherically–Biased Corneal Topography System in Mapping a Radially Aspheric Surface," *Journal of Refractive & Corneal Surgery,* vol. 10, Mar./Apr. 1994, pp. 103–111.

Thorton, "Clinical Evaluation of Corneal Topography," *J. Cataract Refract. Surg.,* vol. 19, Supplement 1993, pp. 198–202.

Rabinowitz, et al., "Computer–assisted Corneal Topography in Keratoconus," *Refractive & Corneal Surgery,* vol 5, Nov./Dec. 1989, pp. 400–408.

Wilson, et al., "Accuracy and Precision of the Corneal Analysis System and the Topographic Modeling System," *Cornea,* vol. 11, No. 1, 1992, pp. 28–35.

Bogan, et al., Computer–assisted Videokeratography of Corneal Topography After Radial Keratotomy, *Arch. Ophthalmol,* vol. 109, Jun. 1991, pp. 834–841.

Bogan, et al., "Classification of Normal Corneal Topography Based on Computer–assisted Videokeratography," *Arch. Ophthalmol,* vol. 108, Jul. 1990, pp. 945–949.

\* cited by examiner

WAVEFRONT SENSOR FOR OBJECTIVE MEASUREMENT OF AN OPTICAL SYSTEM AND ASSOCIATED METHODS

CROSS-REFERENCE TO RELATED APPLICATION

This application claims priority from provisional application Ser. No. 60/198,536, filed Apr. 19, 2000, "Wavefront Sensor with an Extended Dynamic Range and a Small-Format CCD Detector."

BACKGROUND OF THE INVENTION

1. Field of the Invention

The present invention relates to optical measurement systems and methods, and, more particularly, to such systems and methods for objective measurement of an eye.

2. Description of Related Art

Optical systems having a real image focus can receive collimated light and focus it at a point. Such optical systems can be found in nature, e.g., human and animal eyes, or can be manmade, e.g., laboratory systems, guidance systems, and the like. In either case, aberrations in the optical system can affect the system's performance. By way of example, the human eye will be used to explain this problem.

A perfect or ideal eye diffusely reflects an impinging light beam from its retina through the optics of the eye, which includes a lens and a cornea. For such an ideal eye in a relaxed state, i.e., not accommodating to provide near-field focus, reflected light exits the eye as a sequence of plane waves. However, an eye typically has aberrations that cause deformation or distortion of reflected light waves exiting the eye. An aberrated eye diffusely reflects an impinging light beam from its retina through its lens and cornea as a sequence of distorted wavefronts.

There are a number of technologies that attempt to provide the patient with improved visual acuity. Examples of such technologies include remodeling of the cornea using refractive laser surgery or intra-corneal implants, adding synthetic lenses to the optical system using intra-ocular lens implants, and precision-ground spectacles. In each case, the amount of corrective treatment is typically determined by placing spherical and/or cylindrical lenses of known refractive power at the spectacle plane (approximately 1.0–1.5 cms anterior to the cornea) and literally asking the patient which lens or lens combination provides the clearest vision. This is an imprecise measurement of true distortions in the reflected wavefront because (1) a single spherocylindrical compensation is applied across the entire wavefront; (2) vision is tested at discrete intervals (i.e., diopter units) of refractive correction; and (3) subjective determination by the patient is made in order to determine the optical correction. Thus conventional methodology for determining refractive errors in the eye is substantially less accurate than the techniques now available for correcting ocular aberrations.

One method of measuring ocular refractive errors is disclosed in U.S. Pat. No. 5,258,791 to Penney et al. for "Spatially Resolved Objective Autorefractometer," which teaches the use of an autorefractometer to measure the refraction of the eye at numerous discrete locations across the corneal surface. Penney '791 further teaches the use of autorefractometer measurements in determining an appropriate corneal surface reshaping to provide emmetropia, a condition of a normal eye when parallel beams or rays of light are focused exactly on the retina and vision is perfect.

By way of example, one method and system known in the art are disclosed by Junzhong Liang et al. in "Objective Measurement Of Wave Aberrations of the Human Eye with the Use of a Hartmann-Shack Wave-Front Sensor"[*J. Opt. Soc. Am.* 11(7), July 1994, pp 1949–57]. Liang et al. teach the use of a Hartmann-Shack wavefront sensor to measure ocular aberrations by measuring the wavefront emerging from the eye by the retinal reflection of a focused laser light spot on the retina's fovea. The actual wavefront is reconstructed using wavefront estimation with Zernike polynomials. A parallel beam of laser light passes through beam splitters and a lens pair, which brings the beam to a focus point on the retina by the optics of the eye. Possible myopia or hyperopia of the tested eye is corrected by movement of a lens within the lens pair. The focused light on the fovea is then assumed to be diffusely reflected and acts as a point source located on the retina. The reflected light passes through the eye and forms a distorted wavefront in front of the eye that results from the ocular aberrations. The aberrated wavefront is then directed to the wavefront sensor.

The Hartmann-Shack wavefront sensor disclosed by Liang et al. includes two identical layers of cylindrical lenses with the layers arranged so that lenses in each layer are perpendicular to one another, as further disclosed in U.S. Pat. No. 5,062,702 to Bille. In this way, the two layers operate as a two-dimensional array of spherical lenslets that divide the incoming light wave into subapertures. The light through each subaperture is brought to focus in the focal plane of the lens array where a charge-coupled-device (CCD) image module resides.

The system of Liang et al. is calibrated by impinging an ideal plane wave of light on the lenslet array so that a reference or calibrating pattern of focus spots is imaged on the CCD. Since the ideal wavefront is planar, each spot related to the ideal wavefront is located on the optical axis of the corresponding lenslet. When a distorted wavefront passes through the lenslet array, the image spots on the CCD are shifted with respect to a reference pattern generated by the ideal wavefront. Each shift is proportional to a local slope, i.e., partial derivatives of the distorted wavefront, which partial derivatives are used to reconstruct the distorted wavefront, by means of modal wavefront estimation using Zernike polynomials.

However, the system disclosed by Liang et al. is effective only for eyes having fairly good vision. Eyes that exhibit considerable myopia (near-sightedness) cause the focus spots to overlap on the CCD, thereby making local slope determination practically impossible for eyes having this condition. Similarly, eyes that exhibit considerable hyperopia (farsightedness) deflect the focus spots such that they do not impinge on the CCD, thereby again making local slope determination practically impossible for eyes having this condition.

Various embodiments of a method and system for objectively measuring aberrations of optical systems by wavefront analysis have been disclosed in commonly owned application Ser. No. 09/566,668, "Apparatus and Method for Objective Measurement and Correction of Optical Systems Using Wavefront Analysis," filed May 8, 2000, which is hereby incorporated by reference herein. In this invention, an energy source generates a beam of radiation. Optics, disposed in the path of the beam, direct the beam through a focusing optical system (e.g., the eye) that has a rear portion (e.g., the retina) that provides a diffuse reflector. The beam is diffusely reflected back from the rear portion as a wavefront of radiation that passes through the focusing optical system to impinge on the optics. The optics project the wavefront to a wavefront analyzer in direct correspondence with the wavefront as it emerges from the focusing optical system. A wavefront analyzer is disposed in the path of the wavefront projected from the optics and calculates distortions of the wavefront as an estimate of ocular aberrations of the focusing optical system. The wavefront analyzer includes a wavefront sensor coupled to a processor that analyzes the sensor data to reconstruct the wavefront to include the distortions thereof.

A perfectly collimated light beam (i.e., a bundle of parallel light rays, here a small-diameter, eye-safe laser beam) incident on a perfect, ideal emmetropic eye, focuses to a diffraction-limited small spot on the retina. This perfect focusing is true for all light rays passing through the entrance pupil, regardless of position. From the wavefront perspective, the collimated light represents a series of perfect plane waves striking the eye. The light emanates from an illuminated spot on the retina as wavefronts exiting as a series of perfect plane waves, which are directed onto a wavefront analyzer for measuring distortions from ideality.

In one embodiment, the radiation is optical radiation and the wavefront sensor is implemented using a plate and a planar array of light-sensitive cells. The plate is generally opaque but has an array of light-transmissive apertures that selectively let impinging light therethrough. The plate is disposed in the path of the wavefront so that portions of the wavefront pass through the light-transmissive apertures. The planar array of cells is arranged parallel to and spaced apart from the plate by a selected distance. Each portion of the wavefront passing through one of the light-transmissive apertures illuminates a geometric shape covering a unique plurality of cells.

The wavefront optical path relays the re-emitted wavefront from the corneal plane to an entrance face of a Hartman-Shack wavefront sensor. The wavefront incident on the sensor is received by a sensitive charged-coupled-device (CCD) camera and an optical plate containing an array of lenslets. The lenslet array is parallel to the CCD detector face, with a distance therebetween approximately equal to the focal length of each lens in the lenslet array. The lenslet array divides the incoming wavefront into a matching array of "wavelets," each of which focuses to a small spot on the CCD detector plane. The constellation of wavelet spots in the CCD is used to reconstruct the shape of the incident wavefront. Collimated light striking the lenslet at normal (perpendicular) incidence would focus to the spot on the CCD face where this optical axis intersects. The optics of the apparatus provides such collimated light to the wavefront sensor using a calibration optical path.

In the case of a reflected aberrated wavefront, light focuses to a spot displaced from the collimated reference point by a distance $D_x$. The distance from the lenslet face to the CCD surface, $D_z$, is precisely known. Therefore, dividing the measured displacement, $D_x$, by the known propagation distance, $D_z$, the slope of the wavefront at the location of this lens element is determined. The same calculation is applied in the y direction within the plane, and the entire process applied to every lenslet element irradiated by the wavefront. A mathematical algorithm is then applied to reconstruct the wavefront shape consistent with the calculated $D_x/D_z$ and $D_y/D_z$ slope data. Regardless of which wavefront sensor is used, the distance between the planar array of cells and the opaque plate, or the array of lenslets, can be varied to adjust the slope measurement gain of the wavefront sensor and thereby improve the dynamic range of the system.

Another measure of dynamic range enhancement is provided by the focusing optics. The focusing optics includes first and second lenses maintained in fixed positions in the path of the beam and wavefront. An arrangement of optical elements is disposed between the lenses in the path of the beam and the wavefront. The optical elements are adjustable to change the optical path length between the lenses. If an optical correction is desired, the distortions are converted to an optical correction, which, if placed in the path of the wavefront, causes the wavefront to appear approximately as a plane wave. The optical correction can be in the form of a lens or an amount of corneal material ablated from the eye.

One method for determining aberrations of an eye, herein described by way of example, includes directing a probe beam along a probe beam path toward an eye, directing a fixation image along a fixation image path toward the eye, directing a light source along a video image path toward the eye, generating a video image of the eye, directing a wavefront originating from the eye along a wavefront path, wherein the probe beam path, the fixation image path, the video image path, and the wavefront path are coincident at least along a portion of their respective paths, the probe beam path terminating at the retina of the eye and the probe beam reflecting from the retina of the eye as a wavefront, aligning the eye with the probe beam path based at least in part on the video image of the eye generated by the light source directed along the video image path, measuring the wavefront, and generating data representative of the aberrations of the eye based on the measurement of the wavefront. Further, the aligning of the eye with the probe beam path based at least in part on the video image of the eye generated by the light source directed along the video image path, may have the wavefront pass through a single microlens array.

SUMMARY OF THE INVENTION

It is an object of the present invention to provide a system and method for objectively measuring ocular aberrations using a wavefront analyzer of simple and inexpensive design.

It is a further object to provide such an apparatus and method that can employ a small-format camera.

It is an additional object to provide a method for constructing such a system.

These and other objects are achieved by the present invention, a wavefront sensor that comprises an afocal relay stage for magnifying an incoming wavefront reflected from a source plane. In an exemplary application, a retina of an eye reflects an impinging light beam thereon to form a series of wavefronts.

A lenslet array is positioned at a reference plane of the afocal relay stage to receive the magnified wavefront. Further downstream is positioned a means for imaging and demagnifying a focal plane image of the lenslet array at a final image plane. This demagnified image then serves as input to an analyzer, such as, but not intended to be limited to, a charge-coupled-device (CCD) camera.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
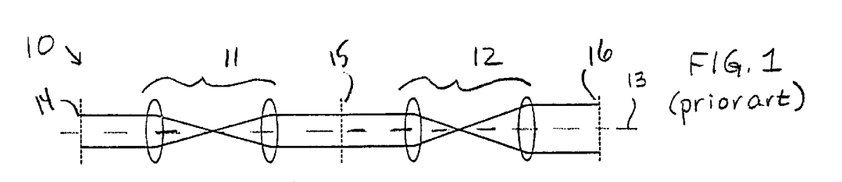
FIG. 1 (prior art) is a schematic diagram of an apparatus for wavefront sensing.
Figure 2:
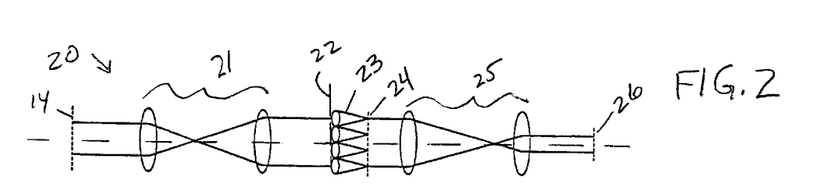
FIG. 2 is a schematic diagram of the apparatus of the present invention for wavefront sensing.

A description of the preferred embodiments of the present invention will now be presented with reference to FIGS. 1 and 2.

The prior art apparatus 10 (FIG. 1) includes a first 11 and a second 12 afocal relay stage within the optical axis 13. The optical path through the first afocal relay stage 11 results in an image of the corneal plane 14 at a first image plane 15, which serves as an insertion point for a spherical trial lens, as described in application Ser. No. 09/566,668.

The wavefront sensor comprises a microlens array plate and a charge-coupled-device (CCD) camera at the second image plane 16 separated by a fixed distance. The optical path 13 thus creates an image of the corneal plane 14 at the lenslet array, that is, at the entrance face of the actual wavefront sensor, which could be accomplished by a single afocal relay stage. Placing a spherical lens into the optical axis 13 at the first image plane 15, in theory, could be used to remove the defocus wavefront error. This would potentially expand the dynamic range of the apparatus 10. However, the trial lens approach is a moving mechanism that can position lenses at the first image plane 15 with tremendous accuracy and repeatability. It was therefore highly desirable that alternative means be developed to address dynamic range.

The present invention 20 (FIG. 2) accomplishes this by magnifying the corneal plane 14 image with the first afocal stage 21. Magnification of the wavefront reduces the wavefront slope, so that the displacement of the focused lights spots on the CCD is decreased. The prior art design 10 does include some magnification in the second afocal stage 12 for this reason. The chosen magnification factor used with that apparatus 10 at the second afocal stage 12 is approximately 1.2, which is insufficient to cover the desired range in refractive errors. A magnification factor in excess of 1.5 is desirable for expanding the use of the apparatus 10. However, simply magnifying the corneal plane 14 has a drawback in that it necessitate a large-aperture wavefront sensor. That is, both the lens array and the CCD camera would preferably have large cross-sectional areas to encompass the magnified image of the point of plane. This is not a significant issue for the lens array plate; however, a large-format CCD camera is quite expensive, and such cameras are only available from a limited number of vendors.

The apparatus 20 of the present invention solves this difficulty. The corneal plane 14 is imaged at a reference plane 22 by the first afocal relay stage 21. The first afocal relay stage 21 magnifies the corneal plane 14 by a predetermined amount. A lenslet array plate 23 is placed at reference plane 22. Focused spots of light from an eye are produced at the lenslet array 23 focal plane 24.

A second afocal relay stage 25 images the array focal plane 24 at a camera plane 26, where the CCD is located. The second stage 25 may be other than an afocal design, but preferably should provide demagnification of the array focal plane 24. This feature permits a small-active-area camera to be used as the light-recording element in the wavefront sensor. Specifics of the optical design are adjustable as desired to maximize performance for given camera and lenslet array specifications.

It may be appreciated by one skilled in the art that additional embodiments may be contemplated, including alternate optical elements to achieve similar functions.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A wavefront sensor comprising:
   an afocal relay stage for magnifying an incoming wavefront reflected from a source plane;
   a lenslet array positioned at a reference plane of the afocal relay stage for receiving the magnified wavefront; and
   means for imaging and demagnifying a focal plane image of the lenslet array at a final image plane, for serving as input to an analyzer.

2. The wavefront sensor recited in claim 1, wherein the imaging and demagnifying means comprises a second afocal relay stage.

3. The wavefront sensor recited in claim 1, wherein the source plane comprises a corneal plane.

4. The wavefront sensor recited in claim 1, wherein the afocal relay stage comprises means for magnifying the incoming wavefront by a factor of at least 1.5.

5. The wavefront sensor recited in claim 1, wherein the demagnifying means is adapted to reduce the lenslet array focal plane image to a dimension smaller than a dimension of the incoming wavefront.

6. A system for determining refractive aberrations of an eye comprising:
   means for directing a beam of light onto a cornea of an eye;
   an afocal relay stage for magnifying wavefronts of light reflected from a retina of the eye;
   a lenslet array positioned at a reference plane of the afocal relay stage for receiving the magnified wavefront;
   means for demagnifying a focal plane image of the lenslet array at a final image plane; and
   means for imaging the final image plane for determining aberrations from planarity of the reflected wavefronts.

7. The system recited in claim 6, wherein the directing means comprises a laser beam focused on a fovea of the eye.

8. The system recited in claim 6, wherein the imaging and demagnifying means comprises a second afocal relay stage.

9. The system recited in claim 6, wherein the afocal relay stage comprises means for magnifying the incoming wavefront by a factor of at least 1.5.

10. The system recited in claim 6, wherein the demagnifying means is adapted to reduce the lenslet array focal plane image to a dimension smaller than a dimension of the incoming wavefront.

11. The system recited in claim 6, wherein the imaging means comprises a charge-coupled-device camera.

12. The system recited in claim 11, wherein the camera comprises a small active area camera.

13. A method of measuring refractive aberrations in an eye comprising the steps of:
   directing a beam of light onto a cornea of an eye;
   magnifying wavefronts of light reflected from a retina of the eye;
   directing the magnified wavefronts to a lenslet array positioned at a reference plane of the magnified wavefronts;
   demagnifying a focal plane image of the lenslet array at a final image plane; and
   imaging the final image plane for determining aberrations from planarity of the reflected wavefronts.

14. The method recited in claim 13, wherein the directing step comprises focusing a laser beam on a fovea of the eye.

15. The method recited in claim 13, wherein the magnifying step comprises directing the reflected wavefronts to a first afocal relay stage.

16. The method recited in claim 13, wherein the demagnifying step comprises directing the focal plane image of the lenslet array to a second afocal relay stage.

17. The method recited in claim 13, wherein the first afocal relay stage comprises means for magnifying the reflected wavefronts by a factor of at least 1.5.

18. The method recited in claim 13, wherein the demagnifying step comprises reducing the lenslet array focal plane image to a dimension smaller than a dimension of the reflected wavefronts.

19. The method recited in claim 13, wherein the imaging step comprises using a charge-coupled-device camera to collect the final image plane.

20. A method for constructing a system for measuring refractive aberrations in an eye comprising the steps of:
   providing means for directing a beam of light onto a cornea of an eye;
   providing means for magnifying wavefronts of light reflected from a retina of the eye;
   providing a lenslet array positioned at a reference plane of the magnified wavefronts;
   providing means for demagnifying a focal plane image of the lenslet array at a final image plane; and
   providing means for imaging the final image plane; and
   providing means for determining aberrations from planarity of the reflected wavefronts.

* * * * *

UNITED STATES PATENT AND TRADEMARK OFFICE
CERTIFICATE OF CORRECTION

PATENT NO.    : 6,578,963 B2
DATED         : June 17, 2003
INVENTOR(S)   : George H. Pettit It is certified that error appears in the above-identified patent and that said Letters Patent is hereby corrected as shown below:

The Title page should be deleted and substitute therefore the attached Title page.

Signed and Sealed this

Twenty-third Day of September, 2003

JAMES E. ROGAN
*Director of the United States Patent and Trademark Office*

(12) United States Patent
Pettit (10) Patent No.: US 6,578,963 B2
(45) Date of Patent: Jun. 17, 2003

(54) WAVEFRONT SENSOR FOR OBJECTIVE MEASUREMENT OF AN OPTICAL SYSTEM AND ASSOCIATED METHODS (75) Inventor: George H. Pettit, Maitland, FL (US)

(73) Assignee: Alcon Universal Ltd., Hunenberg (CH)

( * ) Notice: Subject to any disclaimer, the term of this patent is extended or adjusted under 35 U.S.C. 154(b) by 134 days.

(21) Appl. No.: 09/838,669

(22) Filed: Apr. 19, 2001

(65) Prior Publication Data
US 2002/0003606 A1 Jan. 10, 2002

Related U.S. Application Data
(60) Provisional application No. 60/198,536, filed on Apr. 19, 2000.

(51) Int. Cl.⁷ ............................................. A61B 3/10
(52) U.S. Cl. .................................................. 351/212
(58) Field of Search ................................ 351/211, 212, 351/216, 220, 221; 359/1, 19, 20, 109, 115, 117

(56) References Cited
U.S. PATENT DOCUMENTS

| | | | |
|---|---|---|---|
| 3,679,904 A | * | 7/1972 | Weiner ..................... 359/117 |
| 3,880,501 A | | 4/1975 | Munnerlyn |
| 4,069,823 A | | 1/1978 | Isakov et al. |
| 4,523,821 A | | 6/1985 | Lang et al. |
| 4,579,430 A | | 4/1986 | Bille |
| 4,632,528 A | | 12/1986 | Yoshino et al. |
| 4,669,466 A | | 6/1987 | L'Esperance |
| 4,688,941 A | | 8/1987 | Philbert |
| 4,702,245 A | | 10/1987 | Schröder et al. |
| 4,718,418 A | | 1/1988 | L'Esperance, Jr. |
| 4,721,379 A | | 1/1988 | L'Esperance |
| 4,729,372 A | | 3/1988 | L'Esperance, Jr. |
| 4,750,818 A | | 6/1988 | Cochran |
| 4,764,930 A | | 8/1988 | Bille et al. |
| 4,838,679 A | | 6/1989 | Bille |
| 4,848,340 A | | 7/1989 | Bille et al. |
| 4,881,808 A | | 11/1989 | Bille et al. |

(List continued on next page.)

FOREIGN PATENT DOCUMENTS

| | | |
|---|---|---|
| DE | 42 22 395 A1 | 1/1994 |
| DE | 199 26 476 A1 | 12/2000 |
| EP | 0 697 611 A3 | 2/1996 |
| EP | 0 697 611 A2 | 2/1996 |
| FR | 2 775 779 | 9/1999 |
| JP | 5-146409 | 6/1993 |
| JP | 6-327634 | 11/1994 |
| WO | WO 87/05205 | 9/1987 |
| WO | WO 87/06478 | 11/1987 |
| WO | WO 92/01417 | 2/1992 |
| WO | WO 95/28989 | 11/1995 |
| WO | WO 98/27863 | 7/1998 |

OTHER PUBLICATIONS

Reidy, et al., "Corneal Topography of Epikeratophakia," *Refractive & Corneal Surgery*, vol. 6, Jan./Feb. 1990, pp. 26–31.

Primary Examiner—George Manuel
(74) *Attorney, Agent, or Firm*—Allen, Dyer, Doppelt, Milbrath & Gilchrist, P.A.

(57) ABSTRACT

A wavefront sensor includes an afocal relay stage for magnifying an incoming wavefront reflected from a source plane. In an exemplary application, a retina of an eye reflects an impinging light beam thereon to form a series of wavefronts. A lenslet array is positioned at a reference plane of the afocal relay stage to receive the magnified wavefront. Further downstream is positioned a means for imaging and demagnifying a focal plane image of the lenslet array at a final image plane. This demagnified image then serves as input to an analyzer, such as a charge-coupled-device (CCD) camera.

20 Claims, 1 Drawing Sheet

UNITED STATES PATENT AND TRADEMARK OFFICE
CERTIFICATE OF CORRECTION

PATENT NO. : 6,578,963 B2
DATED : June 17, 2003
INVENTOR(S) : George H. Pettit

It is certified that error appears in the above-identified patent and that said Letters Patent is hereby corrected as shown below:

The Title page should be deleted and substitute therefore the attached Title page.

The attached drawing sheet 1 of 1 should be inserted.

This certificate supersedes Certificate of Correction issued September 23, 2003.

Signed and Sealed this

Ninth Day of December, 2003

JAMES E. ROGAN
*Director of the United States Patent and Trademark Office*

(12) United States Patent
Pettit (10) Patent No.: US 6,578,963 B2
(45) Date of Patent: Jun. 17, 2003

(54) WAVEFRONT SENSOR FOR OBJECTIVE MEASUREMENT OF AN OPTICAL SYSTEM AND ASSOCIATED METHODS

(75) Inventor: George H. Pettit, Maitland, FL (US)

(73) Assignee: Alcon Universal Ltd., Hunenberg (CH)

( * ) Notice: Subject to any disclaimer, the term of this patent is extended or adjusted under 35 U.S.C. 154(b) by 134 days.

(21) Appl. No.: 09/838,669

(22) Filed: Apr. 19, 2001

(65) Prior Publication Data

US 2002/0003606 A1 Jan. 10, 2002

Related U.S. Application Data

(60) Provisional application No. 60/198,536, filed on Apr. 19, 2000.

(51) Int. Cl.$^7$ ................................................. A61B 3/10
(52) U.S. Cl. .................................................. 351/212
(58) Field of Search ............................. 351/211, 212, 351/216, 220, 221; 359/1, 19, 20, 109, 115, 117

(56) References Cited

U.S. PATENT DOCUMENTS

| | | | |
|---|---|---|---|
| 3,679,904 A | * | 7/1972 | Weiner ........................ 359/117 |
| 3,880,501 A | | 4/1975 | Munnerlyn |
| 4,069,823 A | | 1/1978 | Isakov et al. |
| 4,523,821 A | | 6/1985 | Lang et al. |
| 4,579,430 A | | 4/1986 | Bille |
| 4,632,528 A | | 12/1986 | Yoshino et al. |
| 4,669,466 A | | 6/1987 | L'Esperance |
| 4,688,941 A | | 8/1987 | Philbert |
| 4,702,245 A | | 10/1987 | Schröder et al. |
| 4,718,418 A | | 1/1988 | L'Esperance, Jr. |
| 4,721,379 A | | 1/1988 | L'Esperance |
| 4,729,372 A | | 3/1988 | L'Esperance, Jr. |
| 4,750,818 A | | 6/1988 | Cochran |
| 4,764,930 A | | 8/1988 | Bille et al. |
| 4,838,679 A | | 6/1989 | Bille |
| 4,848,340 A | | 7/1989 | Bille et al. |
| 4,881,808 A | | 11/1989 | Bille et al. |

(List continued on next page.)

FOREIGN PATENT DOCUMENTS

| | | |
|---|---|---|
| DE | 42 22 395 A1 | 1/1994 |
| DE | 199 26 476 A1 | 12/2000 |
| EP | 0 697 611 A3 | 2/1996 |
| EP | 0 697 611 A2 | 2/1996 |
| FR | 2 775 779 | 9/1999 |
| JP | 5-146409 | 6/1993 |
| JP | 6-327634 | 11/1994 |
| WO | WO 87/05205 | 9/1987 |
| WO | WO 87/06478 | 11/1987 |
| WO | WO 92/01417 | 2/1992 |
| WO | WO 95/28989 | 11/1995 |
| WO | WO 98/27863 | 7/1998 |

OTHER PUBLICATIONS

Reidy, et al., "Corneal Topography of Epikeratophakia," *Refractive & Corneal Surgery*, vol. 6, Jan./Feb. 1990, pp. 26–31.

*Primary Examiner*—George Manuel
(74) *Attorney, Agent, or Firm*—Allen, Dyer, Doppelt, Milbrath & Gilchrist, P.A.

(57) ABSTRACT

A wavefront sensor includes an afocal relay stage for magnifying an incoming wavefront reflected from a source plane. In an exemplary application, a retina of an eye reflects an impinging light beam thereon to form a series of wavefronts. A lenslet array is positioned at a reference plane of the afocal relay stage to receive the magnified wavefront. Further downstream is positioned a means for imaging and demagnifying a focal plane image of the lenslet array at a final image plane. This demagnified image then serves as input to an analyzer, such as a charge-coupled-device (CCD) camera.

20 Claims, 1 Drawing Sheet

FIG. 1.
(PRIOR ART)

FIG. 2.